United States Patent [19]
Bartels

[11] Patent Number: 4,567,605
[45] Date of Patent: Jan. 28, 1986

[54] X-RAY ANALYSIS APPARATUS COMPRISING A FOUR-CRYSTAL MONOCHROMATOR

[75] Inventor: Willem J. Bartels, Eindhoven, Netherlands

[73] Assignee: U.S. Philips Corporation, New York, N.Y.

[21] Appl. No.: 548,274

[22] Filed: Nov. 3, 1983

[30] Foreign Application Priority Data

Nov. 25, 1982 [NL] Netherlands ............... 8204584

[51] Int. Cl.[4] .................................. G01N 23/20
[52] U.S. Cl. .................................. 378/85; 378/82
[58] Field of Search ............ 378/83, 84, 85, 71, 378/72, 73, 157

[56] References Cited

U.S. PATENT DOCUMENTS 3,518,427  6/1970  Cotterill ........................... 378/84

FOREIGN PATENT DOCUMENTS 0817553  3/1981  U.S.S.R. ........................... 378/73

OTHER PUBLICATIONS

M. Hart, "Crystal Wavelength Calibrators for Synchrotron X-Ray Spectrometers" J. Phys. E: Sci. Instrum., vol. 12, 1979.

Primary Examiner—Craig E. Church
Assistant Examiner—Charles F. Wieland
Attorney, Agent, or Firm—Paul R. Miller

[57] ABSTRACT

In order to achieve high resolution in X-ray analysis, a monochromator comprising four crystals which are pair-wise positioned in parallel orientation is used with the two pairs being positioned in an offset anti-parallel orientation. An X-radiation source may be arranged in the immediate vicinity of the first crystal pair in order to achieve a high beam intensity. Each of the crystal pairs is preferably cut so as to form a U-shape from a single block of a monocrystalline material which is relatively free from dislocations. Germanium is a monocrystalline material of preferred use.

11 Claims, 1 Drawing Figure

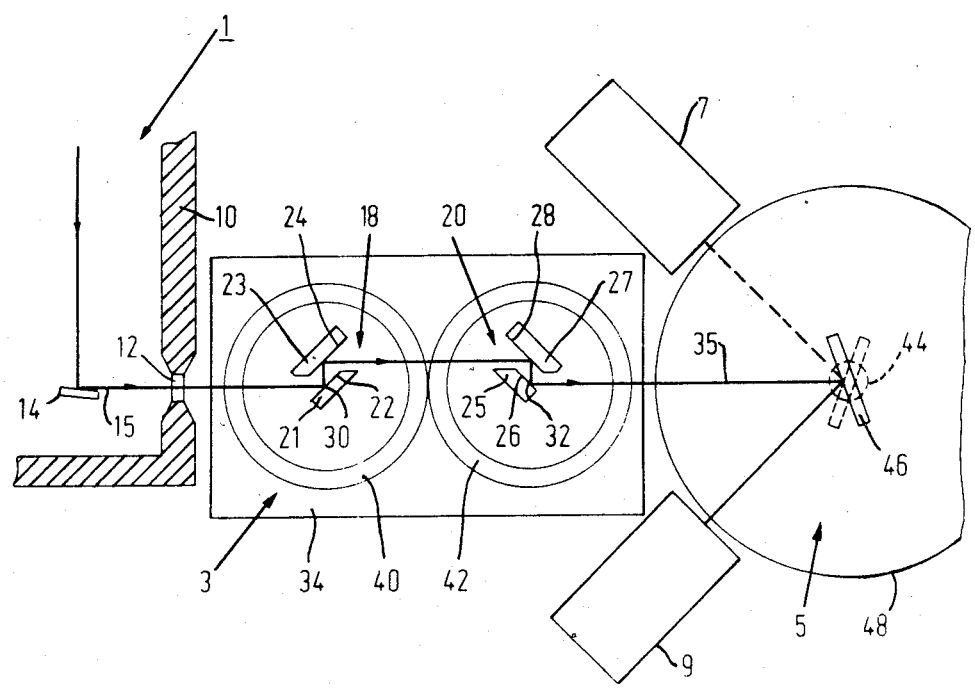

X-RAY ANALYSIS APPARATUS COMPRISING A FOUR-CRYSTAL MONOCHROMATOR

The invention relates to an X-ray analysis apparatus comprising an X-ray source, a monochromator, a specimen holder and an X-ray detector for the detection of X-rays emergent from the specimen.

An X-ray diffractometer comprising a monochromator is known from "Journal of Crystal Growth" 44 (1978), pp. 518-525. An apparatus disclosed therein comprises a first crystal which acts as a monochromator crystal and a second crystal which is formed by a specimen to be analyzed. The crystals are so positioned with respect to one another that the X-ray beam is diffracted in opposite directions by the successive crystals. When the crystals are suitably positioned with respect to one another, the direction of a beam to be ultimately detected will be parallel to the direction of the incident beam. Well-defined diffraction lines can be produced in an apparatus of this kind only if the Bragg angle is the same on both crystals. With such a crystal orientation wavelength-insensitive diffraction can be achieved only in such circumstances. This substantially restricts the usefulness of such an apparatus. Measurements on other crystal surfaces or on a specimen having a different cyrstal structure, each require the use of a corresponding different first crystal. Such an apparatus is not suitable for performing absolute measurements of lattice constants, because at least one of the diffracted beams will always be non-parallel to the incident beam.

This situation is improved by the introduction of a third crystal as proposed in Journal Appl. Crystalography 7 (1974) pp.254–259, because the first two crystals are then positioned in an anti-parallel orientation. Higher-order Bragg diffractions then generate undesired beam directions, so that the displacement path for the detector is inadmissibly restricted for many applications. Problems are also experienced when it is desired to measure radiation having a different wavelength from a different source. Moreover, an excessive amount of the original beam intensity is lost, which results in a signal-to-noise ratio which is too low for measurement signals to be otained satisfactorily.

It is an object of the invention to mitigate these drawbacks; to this end, in accordance with the invention, an X-ray analysis apparatus of the kind set forth is characterized in that the monochromator comprises four analysing crystals which are pair-wise positioned in a mutually parallel orientation and which are adjustable so that the emerging beam remains parallel to the incoming beam.

As a result of using a four-crystal monochromator comprising crystals thus oriented, a high degree of freedom exists with regard to the angle or incidence of the incident X-ray beam; consequently, the apparatus can be constructed so that a comparatively low intensity loss occurs. The middle two crystals of the crystals thus positioned form the actual monochromator The outer two crystals direct the beam so as to conform to a desired path, that is to say to follow an extension of the incident beam, without diminishing the advantages of the beam properties achieved. Wavelength tuning can be achieved by rotating the two crystal pairs in opposite directions while maintaining the parallel disposition of the crystal faces comprising each pair. The ultimate beam direction and position remain unchanged during this rotation. It is to be noted that a four-crystal monochromator is known per se from Physical Review 52 (1937), pp. 872–883, but this monochromator is considered unsuitable for X-ray analysis apparatus because of the optical radiation properties used therein.

A preferred embodiment of the monochromator comprises four germanium monocrystals. These crystals are preferably cut along planes extending parallel to the (440) crystal faces. The two crystal pairs are preferably accommodated in a common housing at a suitable distance from one another for proper mutual adjustment. For the purpose of adjustment each of the crystal pairs may be provided with a friction wheel; these friction wheels can engage one another either directly or indirectly. For exact angular measurement an orientation encoder may be added to at least one rotation mechanism of one of the crystal pairs.

Active crystal surfaces of the crystals in a further preferred embodiment pair-wise form inner surfaces of the limbs of a U-shape cut from a monocrystal. Notably one of the limbs of each of the U-shapes is partly removed, so that a larger amount of clearance is provided for the passage of the beam.

In a high-quality monochromator faces parallel to the (440) crystal faces act as active surfaces. If a slight deterioration of the degree of chromatization is acceptable, faces parallel to the (220) crystal faces can act as active crystal faces in order to achieve a higher radiation intensity.

Some preferred embodiments in accordance with the invention will be described in detail hereinafter with reference to the drawing. The sole FIGURE of the drawing shows diagrammatically an X-ray source 1, a monochromator 3, a goniometer 5, a first detector 7 and a second detector 9 of an X-ray analysis apparatus.

The X-ray source 1 comprises a target 14 which is accommodated in a housing 10 provided with a radiation window 12 and which is made of for example copper, but which may consist of chromium or other customary anode materials. No specific requirements need be imposed on the X-ray source to be used in an X-ray analysis apparatus in accordance with the invention. To provide an optimum intensity for an incident X-ray beam 15, the beam is preferably derived at an angle of from 2° to 5°; to achieve this, the X-ray source is coupled to the monochromator 3 at such an angle.

The monochromator comprises two crystal pairs 18 and 20 which comprise crystals 21, 23, 25 and 27. The crystal faces 22 and 24 of the crystal pair 18 act as active crystal faces. Similarly, the crystal faces 26 and 28 of the crystal pair 20 also act as active crystal faces. The first crystal pair is arranged so as to be rotatable about a shaft 30 which is directed perpendicularly with respect to the plane of drawing and the second crystal pair is similarly rotatable about a shaft 32. The active faces 22 and 24 and the crystal faces 26 and 28 always remain mutually parallel in any rotary position. Therefore, the crystals preferably have, for each pair of crystal faces, a U-shape which is cut from a single monocrystal, the connecting portion of the U being used, for example, for mounting the crystals. The inner surfaces of the limbs of the U form the active crystal faces. After cutting and, if desired, grinding or polishing, a surface layer is removed therefrom, for example, by etching in order to remove material in which stresses might have developed due to mechanical working. A supporting plate 34 for the monochromator has a comparatively heavy construction with the result that, for example, the lower side thereof can be used to support mechanical components required for varying the crystal orientation without the risk of deforming the plate. In the present embodiment, the length of one of the crystals of each of the crystal pairs is reduced so that more clearance exists for a beam path. The attractive properties of the four-crystal monochromator as regards the angle of aperture of the incoming beam enables the X-ray source, provided by a target spot on the anode 14, to be arranged at a minimum distance from the first crystal pair this minimum distance; being determined by the construction of the source. A desirable increase in intensity is thus achieved for the emergent analyzing X-ray beam 35.

The first crystal pair 18 is rotatable about a shaft 30 by a first friction wheel 40 which is situated beneath the mounting plate in this embodiment mounted on the shaft with the said first friction wheel engaging a second friction wheel 42 which is mounted on the shaft 32 about which the second crystal pair 20 is rotatable. However, the two crystal pairs may alternatively be mutually independently adjustable or the adjustment can be performed by means of a drive motor with, for example, programmed settings adapted to the X-ray tube anode material to be used or to the specimens to be analyzed. The crystals are preferably made of germanium having active faces which are parallel to the (440) crystal faces of a germanium monocrystal relatively free from dislocations. By diffraction from the (440) crystal faces an extremely good monochromatic beam having, for example, a relative wavelength width of $2.3 \times 10^{-5}$, a divergence of, for example, 5 arc seconds and an intensity of up to, for example, $3 \times 10^4$ quants per second per cm$^2$, can be formed. Using such a sharply defined beam, errors in lattice spacings of up to 1 in $10^5$ can be measured and high-precision absolute crystal measurements can also be performed. The monochromatization of the X-ray beam is performed in the monochromator by reflection at the middle two crystal faces, i.e. the reflections from the crystal faces 24 and 28. The two reflections from the crystal faces 22 and 26 do not affect the beam parameters but guide the beam 35 in the desired direction so as to coincide with an extension of the incident beam 15. Wavelength adjustment is achieved by rotating the two crystal pairs in mutually opposite directions; during this rotation, the position of the emergent beam 35 does not change.

For measurements requiring a lower degree of monochromatization and divergence, a higher intensity can be achieved by utilizing reflections from (220) crystal faces; a larger spread in wavelength and a larger divergence will then occur, but under the same conditions a beam having an intensity, for example, 30 times greater can be attained. To achieve this when using a germanium crystal, the active crystal faces are cut parallel to the (110) crystal faces.

The monochromator is directly connected to the goniometer 5 on which a specimen 46 to be analyzed is accommodated in a specimen holder 44 in known manner. For detecting radiation emerging from the specimen 46 there are provided detectors 7 and 9 which are rotatable around a goniometer circle 48 in known manner. The detectors enable measurements to be made on the specimen throughout a large angular range and for different orientations of the specimen. For an exact determination of the position of and possibly for repositioning the specimen, the goniometer may include an optical encoder. By combining measurement signals from both detectors, extremely narrow diffraction lines can be defined for all directions, so that lattice constants can be measured both in relative and in absolute terms.

An apparatus of the described kind is particularly suitable for measuring crystal structure and the effects of diffusion, implantation and the like thereon, and also for the exact measurement of epitaxially grown surface layers both in respect of thickness and of composition. The latter measurements are particularly useful in the manufacture of lasers. For X-ray spectrometry measurements, this apparatus, using fixed positions for the specimen and for the detector, can provide an extended spectral range and a substantially higher resolution than is the case for spectrometers known thus far. The apparatus can also be used for the measurement of internal stresses in crystalline materials and, for example, for the determination of the coefficients of expansion of materials, notably for investigating anomalies occurring therein.

What is claimed is:

1. In an X-ray analysis apparatus comprising in order an X-ray source providing an X-ray beam, a monochromator, a specimen holder, and detecting means for detecting X-rays from a specimen on said specimen holder, the improvement comprising said monochromator including
four crystal faces positioned as pairs of crystal faces,
said faces of each pair being parallel to one another,
and said faces being arranged so that an emergent X-ray beam is colinear to an incident X-ray beam,
wherein said pairs are rotatably in a coupled manner to change Bragg angle while maintaining colinearity.

2. An X-ray analysis apparatus according to claim 1, wherein said pairs are rotatable in mutually opposite directions.

3. An X-ray analysis apparatus according to claim 1 or claim 2, wherein said crystal faces are arranged so that reflection at two middle crystal faces achieve monochromatization of said X-ray beam.

4. An X-ray analysis apparatus according to claim 1 or claim 2, wherein each said pair is mechanically connected to a friction wheel, said friction wheel for each pair being mutually engaged for transmitting rotational displacements to said pairs.

5. An X-ray analysis apparatus according to claim 1 or claim 2, wherein each of said pairs of crystal faces is formed of a U-shaped crystal with inner faces of said U-shape acting as said pair of crystal faces.

6. An X-ray analysis apparatus according to claim 5, wherein a portion of a limb of said U-shape has been removed from at least one crystal forming a pair of crystal faces to provide a wider passage for said X-ray beam.

7. An X-ray analysis apparatus according to claim 1 or claim 2, wherein said X-ray source is mounted directly adjacent a supporting plate for supporting said pairs of crystal faces.

8. An X-ray analysis apparatus according to claim 1 or claim 2, wherein said specimen holder forms part of a goniometer, and said detecting means includes two independently movable detectors, said movable detectors being movable with said goniometer.

9. An X-ray analysis apparatus according to claim 1 or claim 2, wherein said crystal faces are formed from dislocation-free germanium monocrystals.

10. An X-ray analysis apparatus according to claim 9, wherein said crystal faces extend parallel to (440) surfaces of germanium.

11. An X-ray analysis apparatus according to claim 9, wherein said crystal faces extend parallel to (110) surfaces of germanium.

* * * * *